United States Patent
Li et al.

(10) Patent No.: US 8,155,734 B2
(45) Date of Patent: Apr. 10, 2012

(54) PROBABILISTIC FUSION IN ARRHYTHMIA DIAGNOSIS AND THERAPY

(75) Inventors: Dan Li, Shoreview, MN (US); Benjamin Ettori, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1755 days.

(21) Appl. No.: 11/379,280

(22) Filed: Apr. 19, 2006

(65) Prior Publication Data

US 2007/0249945 A1 Oct. 25, 2007

(51) Int. Cl.
*A61B 5/0464* (2006.01)

(52) U.S. Cl. ......... 600/518; 600/515; 600/516; 600/517

(58) Field of Classification Search .................. 600/515, 600/516–518; 607/4, 5, 14

See application file for complete search history.

(56) References Cited

U.S. PATENT DOCUMENTS

| | | | |
|---|---|---|---|
| 6,317,632 B1 | 11/2001 | Krig et al. | |
| 6,456,871 B1* | 9/2002 | Hsu et al. | 600/518 |
| 6,522,925 B1 | 2/2003 | Gilkerson et al. | |
| 6,526,313 B2 | 2/2003 | Sweeney et al. | |
| 6,708,058 B2 | 3/2004 | Kim et al. | |
| 6,728,572 B2 | 4/2004 | Hsu et al. | |
| 6,801,802 B2 | 10/2004 | Sitzman et al. | |
| 2001/0001808 A1 | 5/2001 | Chassaing et al. | |
| 2001/0034488 A1 | 10/2001 | Policker et al. | |
| 2003/0120316 A1* | 6/2003 | Spinelli et al. | 607/14 |
| 2004/0093035 A1* | 5/2004 | Schwartz et al. | 607/5 |
| 2004/0167579 A1* | 8/2004 | Sharma et al. | 607/14 |
| 2004/0220465 A1 | 11/2004 | Cafarella | |
| 2005/0010257 A1 | 1/2005 | Lincoln et al. | |
| 2005/0021097 A1 | 1/2005 | Thompson et al. | |
| 2005/0124901 A1 | 6/2005 | Misczynski et al. | |

OTHER PUBLICATIONS

Baek, W., et al., "Optimal m-ary data fusion with distributed sensors", *IEEE Transactions on Aerospace and Electronic Systems*, 31(3), (1995), 1150-1152.

Chair, Z., et al., "Optimal data fusion in multiple sensor detection systems", *IEEE Transactions on Aerospace and Electronic Systems*. AES-22, (1986), 98-101.

Dorian, P., et al., "Randomized controlled study of detection enhancements versus rate-only detection to prevent inappropriate therapy in a dual-chamber implantable cardioverter-defibrillator", *Heart Rhythm*, 1(5), (2004), 540-547.

Gold, M. R., et al., "Advanced Rhythm Discrimination for Implantable Cardioverter Defibrillators Using Electrogram Vector Timing and Correlation", *Journal of Cardiovascular Electrophysiology*, 13(11) (2002), 1092-1097.

(Continued)

*Primary Examiner* — Niketa Patel
*Assistant Examiner* — Hiba El-Kaissi
(74) *Attorney, Agent, or Firm* — Schwegman, Lundberg & Woessner, P.A.

(57) ABSTRACT

This document describes, among other things, systems and methods for characterizing a tachyarrhythmia. A method comprises obtaining a current first primary characterization of the tachyarrhythmia and a current first primary confidence level of the current first primary characterization, obtaining a current second primary characterization of the tachyarrhythmia and a current second primary confidence level of the current second primary characterization, and determining a current secondary characterization using the current first primary characterization, the current first primary confidence level, the current second primary characterization, and the current second primary confidence level.

29 Claims, 7 Drawing Sheets

OTHER PUBLICATIONS

Hernandez, A. I., et al., "Multisensor Fusion for Atrial and Ventricular Activity Detection in Coronary Care Monitoring", *IEEE Transactions on Biomedical Engineering*, 46(10), (1999), 1186-1190.

Mansouri, N., et al., "Simple Counting Rule for Optimal Data Fusion", *Proceedings of 2003 IEEE Conference on Control Applications*, (2003), 1186-1191.

* cited by examiner

PROBABILISTIC FUSION IN ARRHYTHMIA DIAGNOSIS AND THERAPY

TECHNICAL FIELD

The field generally relates to implantable medical devices and, in particular, but not by way of limitation, to systems and methods for probabilistic fusion in arrhythmia diagnosis and therapy.

BACKGROUND

Implantable medical devices (IMDs) are devices designed to be implanted into a patient. Some examples of these devices include cardiac function management (CFM) devices. CFMs include implantable pacemakers, implantable cardioverter defibrillators (ICDs), cardiac resynchronization therapy devices, and devices that include a combination of such capabilities. The devices are typically used to treat patients using electrical therapy and to aid a physician or caregiver in patient diagnosis through internal monitoring of a patient's condition. The devices may include electrical leads or other electrodes in communication with sense amplifiers to monitor electrical heart activity within a patient, and often include sensors to monitor other internal patient parameters. Other examples of implantable medical devices include implantable insulin pumps or devices implanted to administer drugs to a patient.

Additionally, some IMDs detect events by monitoring electrical heart activity signals. In CFM devices, these cardiac signals typically include depolarizations indicative of heart chamber contractions or repolarizations indicative of heart chamber expansions. By monitoring cardiac signals indicative of expansions or contractions, some IMDs are able to detect a tachyarrhythmia. Such IMDs typically provide therapy for tachyarrhythmia, such as high energy shock therapy or anti-tachycardia pacing (ATP). Tachyarrhythmia includes abnormally rapid heart rate, referred to as tachycardia, including ventricular tachycardia (VT) and supraventricular tachycardia (SVT), or even incoherent fibrillation.

Typically, arrhythmia detection and therapy decisions in current implantable medical devices (IMDs) are solely based on intra-cardiac electrogram (EGM) information, such as the duration of cardiac cycle intervals or morphology of detected depolarizations. A typical interval-based method compares the time interval between successive depolarizations (or, inversely, a rate-based method compares heart rate) to various zones to discriminate between or classify tachyarrhythmias. A morphology-based method typically compares the shape of a cardiac depolarization to a morphology template to discriminate between or classify tachyarrhythmias.

SUMMARY

To determine a diagnosis and an appropriate therapy, the methods described above are typically implemented with a static decision tree that uses the EGM information. Although simple in implementation, a static decision tree may not account for variations between patients or variations within a patient. Furthermore, a static decision tree is likely unable to take into account the effectiveness of the detection modules. Also, static decision trees that only consider EGM signals may not be sufficient to determine an appropriate anti-tachyarrhythmia therapy.

Because of these limitations, the present inventors have recognized a need for improved tachyarrhythmia detection, discrimination, and therapy. The present inventors have determined, among other things, that using a dynamically-updated probabilistic network comprising multiple different information sources can increase the accuracy of arrhythmia discrimination and improve therapy efficacy.

According to one example, there is a method for characterizing a tachyarrhythmia, the method comprising obtaining a current first primary characterization of the tachyarrhythmia and a current first primary confidence level of the current first primary characterization; obtaining a current second primary characterization of the tachyarrhythmia and a current second primary confidence level of the current second primary characterization; and determining a current secondary characterization using the current first primary characterization, the current first primary confidence level, the current second primary characterization, and the current second primary confidence level.

According to another example, there is a method for characterizing a tachyarrhythmia, the method comprising obtaining a first primary characterization of the tachyarrhythmia and a first primary confidence level of the first primary characterization; obtaining a second primary characterization of the tachyarrhythmia and a second primary confidence level of the second primary characterization; obtaining a third primary characterization of the tachyarrhythmia and a third primary confidence level of the third primary characterization; obtaining a fourth primary characterization of the tachyarrhythmia and a fourth primary confidence level of the fourth primary characterization; determining a first secondary characterization using the first primary characterization, the first primary confidence level, the second primary characterization, and the second primary confidence level; and determining a second secondary characterization using the third primary characterization, the third primary confidence level, the fourth primary characterization, and the fourth primary confidence level.

According to another example, there is a method for characterizing a tachyarrhythmia, the method comprising obtaining a first primary characterization of the tachyarrhythmia and a first primary confidence level of the first primary characterization; obtaining a second primary characterization of the tachyarrhythmia and a second primary confidence level of the second primary characterization; obtaining a third primary characterization of the tachyarrhythmia and a third primary confidence level of the third primary characterization; obtaining a fourth primary characterization of the tachyarrhythmia and a fourth primary confidence level of the fourth primary characterization; determining a first secondary characterization using the first primary characterization, the first primary confidence level, the second primary characterization, and the second primary confidence level; determining a second secondary characterization using the third primary characterization, the third primary confidence level, the fourth primary characterization, and the fourth primary confidence level; determining a first therapy decision using the first secondary characterization; determining a second therapy decision using the second secondary characterization; and determining a tertiary therapy decision using the first and second therapy decisions.

According to another example, there is a method for characterizing a tachyarrhythmia, the method comprising obtaining a current first primary characterization of the tachyarrhythmia and a current first primary confidence level of the current first primary characterization, wherein the current first primary confidence level is based at least in part on an accuracy of a previous first primary characterization; obtaining a current second primary characterization of the tachyarrhythmia and a current second primary confidence level of the current second primary characterization, wherein the current second primary confidence level is based at least in part on an accuracy of a previous second primary characterization; determining a current secondary characterization using the current first primary characterization, the current first primary confidence level, the current second primary characterization, the current second primary confidence level, and an independent weight factor, wherein the independent weight factor is a function of a therapy history accuracy and a probable characterization, wherein the probable characterization is based on a correlation between a patient's one or more indications and a population database. In some examples, the population database comprises statistics and data from a broad spectrum of patients with similar diseases.

According to another example, there is a system for characterizing a tachyarrhythmia, the system comprising one or more sensors, wherein each sensor detects at least one biological indication; two or more detectors, where each detector is coupled to at least one sensor, wherein each detector is capable of using signals from at least one sensor to determine a local characterization an arrhythmia; and a fusion machine, wherein the fusion machine comprises a fusion module coupled to the detectors, wherein the fusion module is capable of determining a fused characterization using the local characterizations of the detectors; a weight updater module coupled to the fusion module and to the detectors, wherein the weight updater module is capable of determining an accuracy using at least in part the local characterizations and the fused characterization, calculating necessary adjustments to one or more weights, and providing the one or more weights to the detectors and the fusion module; and an independent weight generator module coupled to the fusion module, a population database, and the detectors, wherein the independent weight generator module is capable of determining an independent weight using at least in part, information from the population database and providing the independent weight to the fusion module and the detectors.

According to another example, there is a computer-readable medium including instructions that, when performed by a computer, cause the computer to obtain a current first primary characterization of a tachyarrhythmia and a current first primary confidence level of the current first primary characterization; obtain a current second primary characterization of the tachyarrhythmia and a current second primary confidence level of the current second primary characterization; determine a current secondary characterization using the current first primary characterization, the current first primary confidence level, the current second primary characterization, and the current second primary confidence level.

According to another example, there is a computer-readable medium including instructions that, when performed by a computer, cause the computer to obtain a first primary characterization of the tachyarrhythmia and a first primary confidence level of the first primary characterization; obtain a second primary characterization of the tachyarrhythmia and a second primary confidence level of the second primary characterization; obtain a third primary characterization of the tachyarrhythmia and a third primary confidence level of the third primary characterization; obtain a fourth primary characterization of the tachyarrhythmia and a fourth primary confidence level of the fourth primary characterization; determine a first secondary characterization using the first primary characterization, the first primary confidence level, the second primary characterization, and the second primary confidence level; determine a second secondary characterization using the third primary characterization, the third primary confidence level, the fourth primary characterization, and the fourth primary confidence level; and determine a tertiary characterization using the first and second secondary characterizations.

This summary is intended to provide an overview of certain subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Introduction

Figure 1:
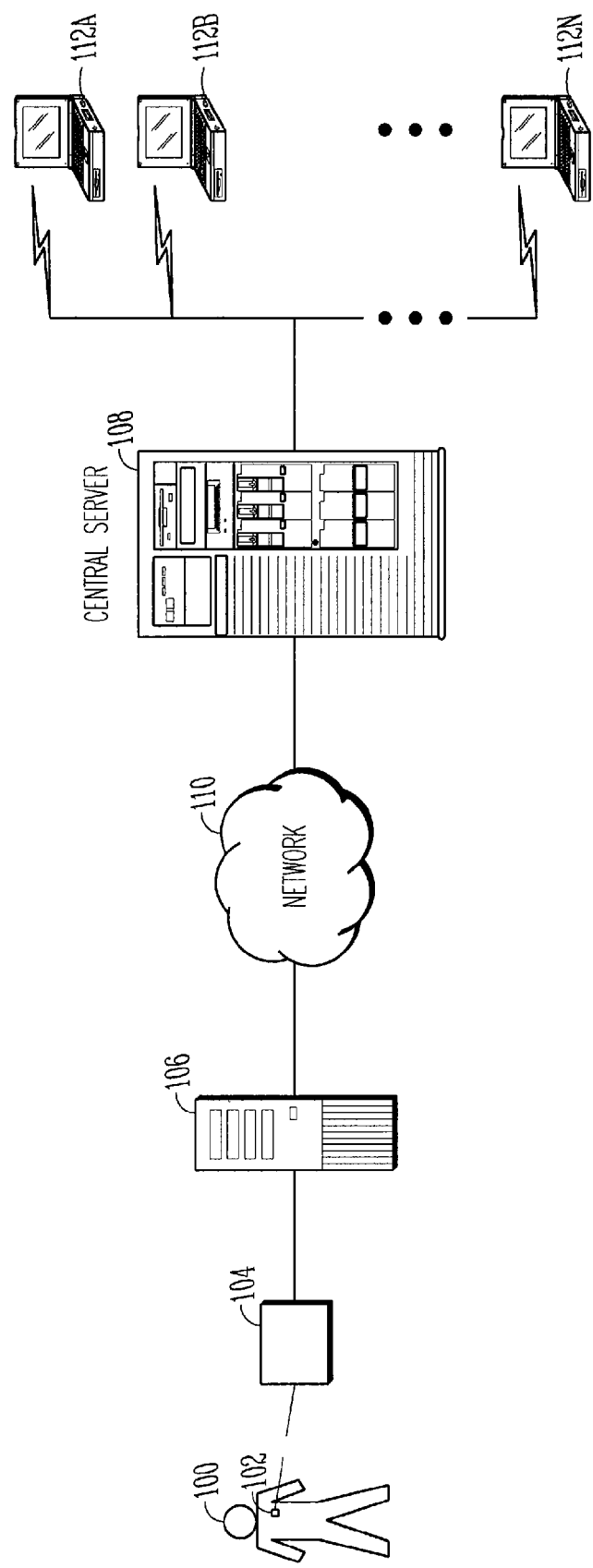
FIG. 1 is a schematic view illustrating portions of a system that characterizes and records arrhythmia diagnosis and therapy.

FIG. 1 is a schematic view illustrating portions of a system that characterizes and records an arrhythmia or a device's response to an arrhythmia. In the example of FIG. 1, a patient 100 is provided with an IMD 102. In some examples, the IMD 102 is capable of characterizing an arrhythmia. The IMD 102 communicates with an external transceiver 104. Typically, the IMD 102 receives commands from the transceiver 104. In some examples, the IMD 102 can transfer one or more characterizations of an arrhythmia to the transceiver 104. In other examples, the IMD 102 communicates raw signal data to the transceiver 104, which may then communicate the signal data to another computer for processing. Typically, the transceiver 104 is located in close proximity to the patient 100. The transceiver 104 may be included within a personal computer or a specialized device, such as a programmer. In one example, the transceiver 104 is a hand-held device that is capable of being connected to a local computer 106. Typically, the connection can be made using a hard-wired connection (e.g., serial, USB, Firewire) or a wireless connection (e.g., RF, IR). In certain examples, the local computer 106 is adapted to communicate with a remote computer 108. The communication link between the local computer 106 and the remote computer 108 is typically made through a wide-area network 110, such as the Internet. In certain examples, one or more terminals 112A, 112B, ..., 112N are connected to the remote computer 108. Typically, a user may connect to the remote computer 108 using a terminal 112 to query a history of characterizations, to initiate commands that administer therapy or program the transceiver 104, or to provide another characterization of an arrhythmia based on the user's experience, patient indications, or other sources. In certain examples, the user-provided characterization is communicated to the transceiver 104 for use in future characterizations.

EXAMPLES

Figure 2:
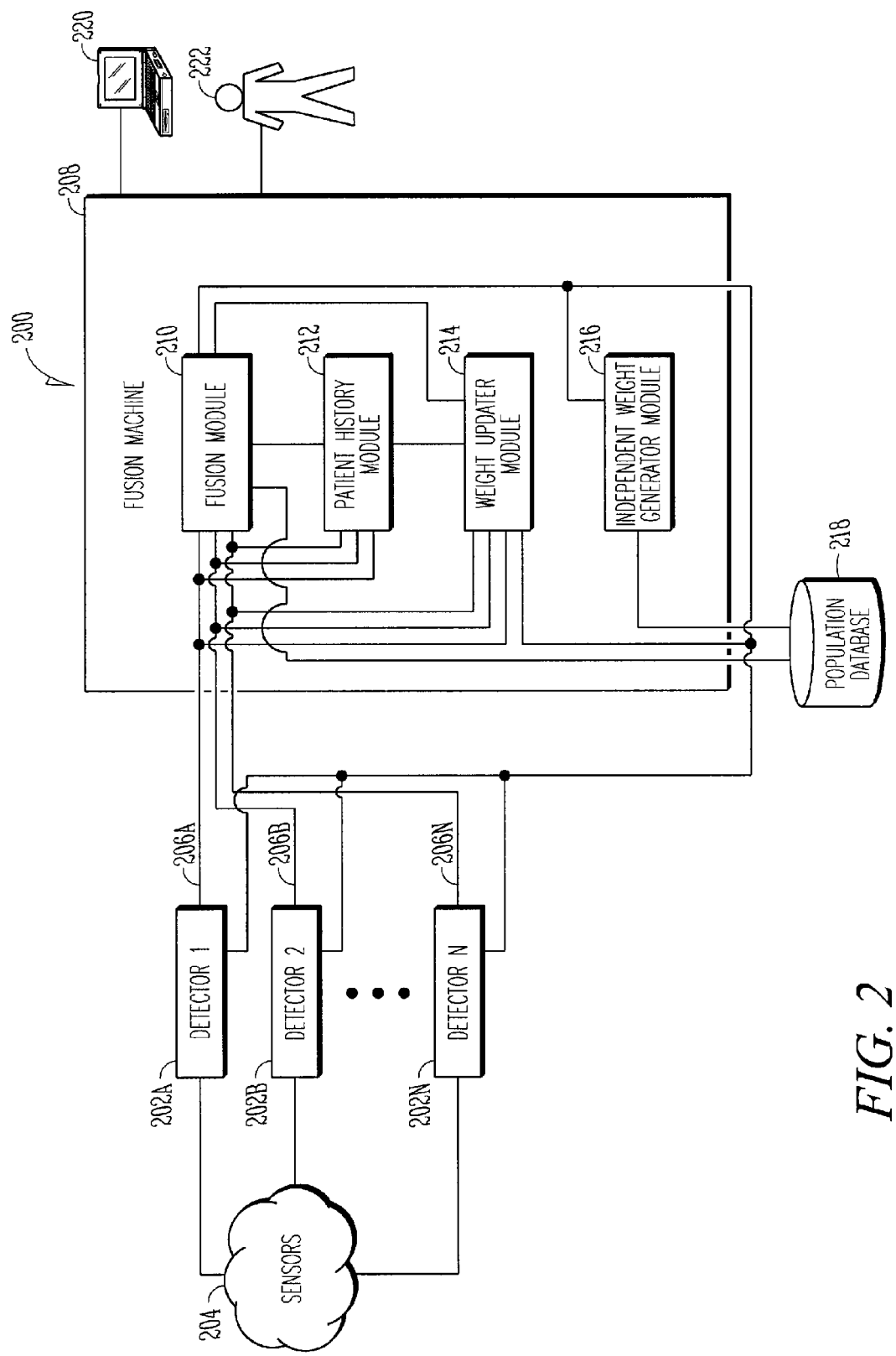
FIG. 2 is a detailed schematic view illustrating portions of a system that characterizes and records arrhythmia diagnosis and therapy.

FIG. 2 is a detailed schematic view illustrating portions of a system 200 that characterizes and records arrhythmia diagnosis and therapy. In the system 200, two or more detectors 202A, 202B, ..., 202N are connected to one or more sensors 204. Examples of the sensors 204 include, without limitation, an electrocardiogram, an accelerometer, a pressure sensor, a cardiac output (CO) detector, and a microphone. Each detector 202 can include hardware and software to evaluate the one or more input signals from the one or more sensors 204 to characterize or classify an arrhythmia episode or a particular aspect of an arrhythmia episode. Each characterization, along with a value representing a confidence level, is communicated to a fusion machine 208 using a corresponding data pathway 206A, 206B, ..., 206N. Depending on the configuration of the detectors 202 and the fusion machine 208, the corresponding data pathways 206 could be wired or wireless. For example, in certain examples, the detectors 202 and the fusion machine 208 are integrated into an IMD. However, because certain information is not typically available to an IMD, one or more detectors 202 could be located away from the IMD and possibly separate from each other. In this case, the fusion machine 208 could be integrated into the same machine as a detector 202 or it could be a separate machine.

The two or more detectors 202 communicate their primary characterizations and confidence levels to a fusion module 210. The fusion module 210 generates a secondary characterization based on a combination of the primary characterizations. In certain examples, the primary characterizations are combined along with the corresponding confidence levels using a probabilistic fusion method to calculate a secondary characterization.

In certain examples, the secondary characterization is saved into the patient history module 212. In certain examples, the patient history module 212 also collects raw data, including one or more patient indications, from the detectors 202. In other examples, patient indications are provided to the patient history module 212 from an independent channel, such as a user input. This raw data, along with any secondary characterizations, is made available to an external user 222, such as a physician, via a computer 220, which can access the fusion machine 208. In certain examples, the user 222 is able to occasionally read previous primary and secondary characterizations and input a tertiary characterization based on the user's personal observations and conclusions. This tertiary characterization is typically derived independently from the decision-making process that generated the secondary characterization. In some examples, the tertiary characterization is stored in the patient history module 212 for future reference. The tertiary characterization is then used by the weight updater module 214, which compares the user-generated tertiary characterization with the fusion-based secondary characterization and generates adjustments to two or more weight values. The weights are typically reflections of the efficacy or reliability of the detectors 202 and are used, at least in part, to compute the confidence levels. The updated weights are occasionally communicated to the detectors 202, such as via the data pathways 206.

In certain examples, an independent weight is generated by the independent weight generator module 216. Typically, the independent weight represents a prior probability of a particular type of arrhythmia based on the patient's history in reference to a population domain. The independent weight generator module 216 calculates the independent weight by using a combination of patient indications, which may be provided by the detectors 202 or by an independent channel, such as user input; records from a population database 218 that correspond with the patient indications; and therapy history provided by the patient history module 212. In certain examples, the independent weight is used by the fusion module 210 when calculating the secondary (fused) characterization.

Figure 3:
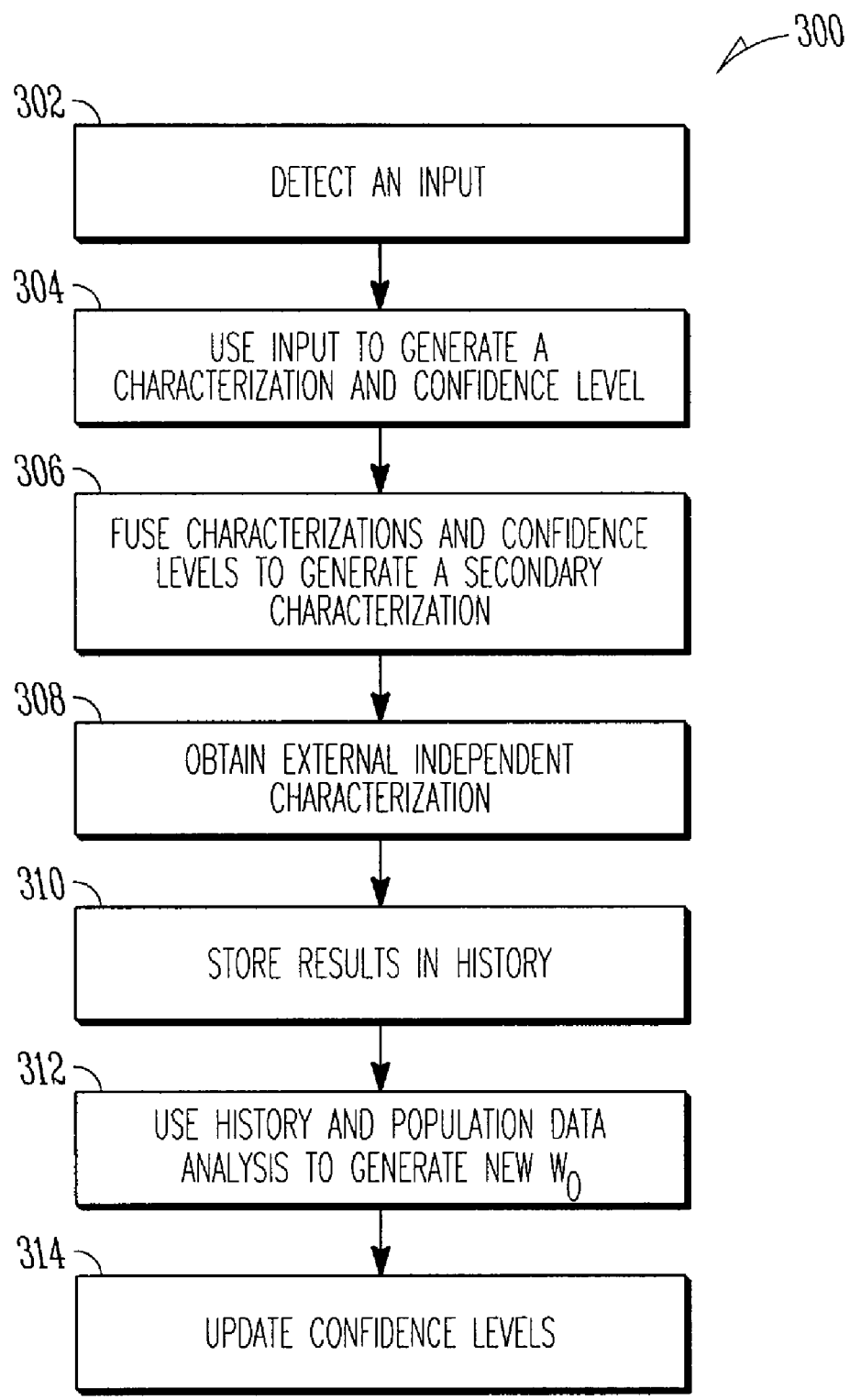
FIG. 3 is a flowchart illustrating generally a method of characterizing and recording arrhythmia diagnosis and therapy.

FIG. 3 is a flowchart illustrating generally a method 300 of characterizing and recording arrhythmia diagnosis and therapy. At 302, one or more signals $x_1, x_2, \ldots, x_n$ are detected. The signals are typically generated from an electrical or physical detector, such as electrocardiogram (EGM), an accelerometer, a pressure sensor, a cardiac output (CO) detector, a microphone, or any other device that is capable of detecting biological indications.

At 304, two or more of the signals are used to generate a characterization of the tachyarrhythmia. In certain examples, one or more functions $g_1(x), g_2(x), \ldots, g_n(x)$ use the detected signals $x_1, x_2, \ldots, x_n$ to generate a primary characterization of a tachyarrhythmia, such that $g_n(x)=(u_n, w_n)$, where $u_n$ is a characterization (or an aspect of a characterization) and $w_n$ is the weight or probability (i.e., confidence level) that $u_n$ is the correct characterization. For an initial characterization calculation, each weight value can be initialized to provide an initial desired weighting between each function $g_1(x), g_2(x), \ldots, g_n(x)$. As the method 300 proceeds through successive iterations, each such seeded weight value is adaptively updated, as described below at 314, to properly indicate an increased or decreased confidence level after each characterization is verified. The functions $g_1(x), g_2(x), \ldots, g_n(x)$ can use signals $x_1, x_2, \ldots, x_n$ either alone or in combination. For example, a rate-based detection function may only use signals from an EGM, whereas an "S1 heart sound amplitude" function may use signals from both an EGM and an accelerometer.

At 306, the primary characterizations are fused, or combined, to calculate a secondary characterization. In particular, the set of primary characterizations and confidence levels $\{(u_1,w_1), (u_2,w_2), \ldots, (u_n,w_n)\}$ are typically combined using a probabilistic fusion function $f$ to obtain a secondary characterization v, such that $v=f(\{u_i,w_i\}_{i=1:n})$ In one example, the fusion method implemented is the Chair-Varshney method:

$$f(\{u_i, w_i\}_{i=1:n}) = w_0 + \sum_{k=1}^{n} w_k u_k \begin{cases} > 0:H_1 \\ \leq 0:H_0 \end{cases}$$

$$w_0 = \log(P_1/P_0)$$

$$w_k = \begin{cases} \log(P_{Dk}/P_{Fk}) = \log(TP_k/FP_k) - w_0 & u_k = +1 \\ \log[(1-P_{Fk})/(1-P_{Dk})] = \log(TN_k/FN_k) + w_0 & u_k = -1 \end{cases}$$

where $H_1$ and $H_0$ are two mutually exclusive hypotheses, such as the characterizations VT and SVT; $u_k$ is the decision made by detector k, using values of 1 (e.g., to indicate VT) or −1 (e.g., to indicate SVT); $P_1$ and $P_0$ are the patient's prior probability of VT and SVT; $P_{Dk}$ and $P_{Fk}$ are probabilities of detection and false alarm for detector k; and $TP_k$, $TN_k$, $FP_k$, and $FN_k$ are number of true positive, true negative, false positive, and false negative episodes that detector k has previously identified.

The value of $w_0$ is typically based on a prior probability. During an initial characterization, in some examples, when no prior probabilities have been calculated, the value of $w_0$ is initially undefined and is therefore initially not used as a factor in the fusion formula. In later characterizations, the past performance of the fusion formula is used to determine the value of $w_0$. An example of this is described below in further detail at 312.

At 308, an independent characterization is obtained. This independent characterization can be referred to as a "tertiary" characterization, for convenience, to distinguish it from the primary and secondary characterizations discussed above. In one example, the tertiary characterization is used to determine the accuracy of the secondary characterization. Typically, the tertiary characterization is provided by a doctor or an attending medical professional who will occasionally or periodically review the patient's indications to determine a tachyarrhythmia characterization. In some examples, the tertiary characterization is saved for future reference. Ideally, a physician or other medical professional can provide a tertiary characterization for comparison every time a secondary (fused) characterization is generated. However, when a user is unavailable to provide a tertiary characterization, in order to provide dynamically updated confidence levels, in some examples, the secondary (fused) characterization is used as a tertiary (reference) characterization.

At 310, the current secondary characterization is stored. In this example, the secondary (fused) characterization is referenced as a portion of the patient's history, as discussed at 312 below, and optionally used to calculate new confidence levels, such as described at 314 below.

At 312, the method 300 uses one or more of the patient's indications to determine a population-based prior probability of either characterization (e.g., VT or SVT). In certain examples, the history of secondary characterizations is used as a portion of the patient's relevant history. Generally, patient indications typically include vital signs, arrhythmia history, or risk factors, such as weight, age, or family history. One or more of these indications can be retrieved from a patient database or from one or more sensors monitoring the patient.

The patient's indications are used to determine a probability that the current secondary (fused) characterization is accurate. In effect, this probability can act as another reference characterization, similar to the tertiary characterization discussed above at 308. To determine the population-based prior probability, the method 300 can use a population database and the patient's indications to determine the probability of each possible characterization. In general, let $\overline{P}_0$ be the probability that a person in the population database with the current patient's indications could have the first characterization (e.g., SVT) and let $\overline{P}_1$ be the probability that a person in the population database with the current patient's indications could have the second characterization (e.g., VT). Then, a patient's probability of experiencing one or the other characterizations based on a population can be expressed as:

$$P_0 = \frac{k_0 + m \cdot \overline{P}_0}{k_0 + k_1 + m},$$

$$P_1 = \frac{k_1 + m \cdot \overline{P}_1}{k_0 + k_1 + m} \Rightarrow w_0 = \log\left(\frac{P_1}{P_0}\right) = \log\left(\frac{k_1 + m \cdot \overline{P}_1}{k_0 + m \cdot \overline{P}_0}\right)$$

where $\overline{P}_1$ and $\overline{P}_0$ are population-based prior probabilities of VT and SVT, respectively, which could be determined from subset of patients with similar medical history and indications; $k_1$ and $k_0$ are the respective number of VT and SVT episodes that the present patient has experienced; and m is a constant that controls the impact of $\overline{P}_1$ and $\overline{P}_0$ on $P_1$ and $P_0$. In general, this is referred to as the "m-estimate of probability." A larger m will adjust the patient's prior probabilities more towards the population-wise statistics. Inclusion of $\overline{P}_1$ and $\overline{P}_0$ in the computation is useful when the number of observed episodes k is too small to yield a robust estimate of the prior probabilities. In certain examples, the value of m is adaptively changed based on the number of episodes k.

At 314, the confidence levels are updated. In particular, the confidence levels are typically updated by comparing the primary characterizations to a reference characterization. For example, the confidence level $w_n$ is lowered if the primary characterization $u_n$ was deemed inaccurate (by comparing it to a reference characterization) and the confidence level is raised if the primary characterization was deemed accurate. Other methods to raise or lower the confidence level based on previous results could be used. For example, the confidence level could be adaptively adjusted, such as based on external readings of noise, known limitations of a detector's circuitry, or other physical factors that could affect the reliability of a characterization.

In particular, in this example, each confidence level (weight) is updated based on the formula described in the discussion of 306 above. Using the tertiary characterization as a reference characterization, or alternatively the secondary characterization, the method 300 can calculate values for the probabilities of detection $P_{Dk}$ and false alarm $P_{Fk}$, and the number of true positives $TP_k$, true negatives $TN_k$, false positives $FP_k$, and false negative $FN_k$ episodes each detector has identified. Additionally, using the values for $P_0$ and $P_1$ calculated at 312, an updated value for the independent weight $w_0$ is available. The new confidence levels are typically communicated occasionally or periodically to the detectors, such as to update the individual weights $w_n$ in future primary characterizations.

Figure 4:
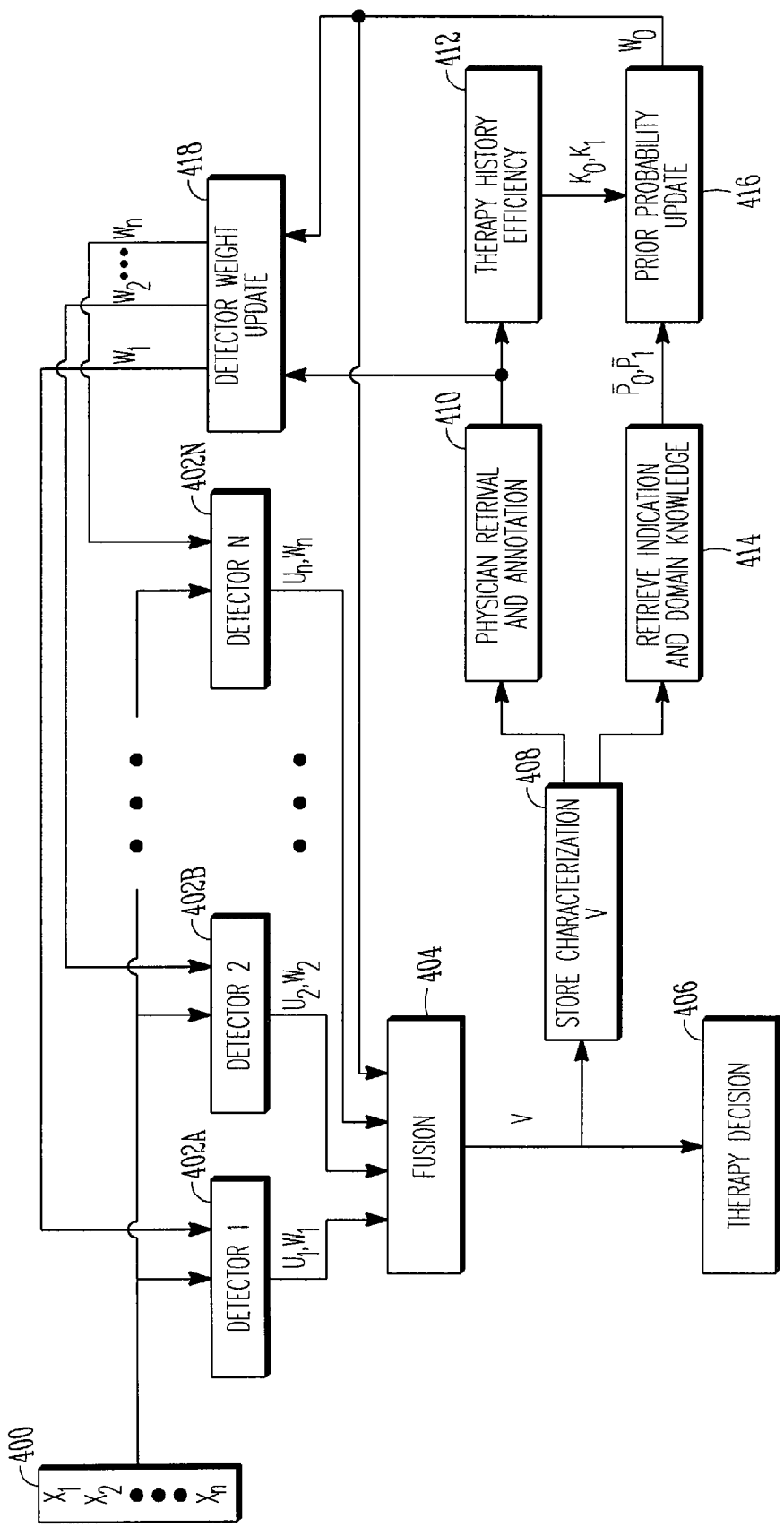
FIG. 4 is a schematic diagram illustrating generally a method of characterizing and recording arrhythmia diagnosis and therapy.

FIG. 4 is a schematic diagram illustrating generally the method 300 of classifying and reporting arrhythmia diagnosis and therapy. At 400, one or more signals are available from one or more sensors (not shown). Examples of typical signals include, without limitation, an electrogram (EGM), an intracardiac or thoracic impedance signal, an accelerometer signal, or a microphone sound signal. Detectors 402A, 402B, . . . , 402N use the one or more signals 400 in one or more various detection methods, such as a rate or interval-based arrhythmia discrimination method or a morphology-based arrhythmia discrimination method. Each detector 402 typically outputs a primary characterization $u_n$ and a probability value (i.e., confidence level) $w_n$ of the decision. The primary characterizations and confidence levels are fused at 404, such as by using a fusion formula $f$. In one example, the fusion formula is based on the Chair-Varshney technique, as described above. The secondary fused characterization v is used, in certain examples, to provide a therapy decision at 406. Typical therapies include an atrial or ventricular defibrillation shock or anti-tachyarrhythmia pacing (ATP). The secondary characterization is typically also stored in some memory at 408, such as for future reference. At 410, a user (e.g., a physician) retrieves the secondary characterization v, such as to evaluate it. In one example, the user annotates the secondary characterization, such as for later access by the same or another user. Typically, the user will provide an independent characterization (a tertiary characterization). At 412, the number of episodes of VT and SVT are calculated using the tertiary characterization. A counting method using a stored counter value is used in one example. In certain examples, such as when a user is unavailable to provide a tertiary characterization, the secondary fused characterization can be used a reference. The number of episodes of VT and SVT are made available to other steps in the process. At 414, the patient's indications, medical history, arrhythmia history, and other information are used to determine a population-based prior probability of VT and SVT ($\overline{P}_1$ and $\overline{P}_0$), which could be determined from a subset of patients with similar medical histories and indications (e.g., using a population database). At 416, the population-based probabilities ($\overline{P}_1$, $\overline{P}_0$) are used along with the number of episodes of VT and SVT that the patient has experienced ($k_1$, $k_0$), to calculate a probability of each type of arrhythmia based on the patient's indications in their arrhythmia history and population data. These probabilities are used to calculate a new independent weight $w_0$, which is typically provided to both the fusion function 404 and to update the detector weights at 418. In particular, at 418, each detector's 402 weight (confidence level) is updated. In certain examples, a detector's confidence level is raised when the secondary characterization is similar or matches the detector's primary characterization. Conversely, the confidence level is lowered if the secondary characterization is not similar or does not match the primary characterization. The newly computed confidence levels are occasionally or periodically provided to one or more of the detectors 402, such as for use in the next iteration of the method 300.

Examples of Single and Multi-Level Detection Schemes

The method 300 can be used in several configurations. Each configuration typically uses one or more sensors and one or more detectors, which discriminate the tachyarrhythmia based on the sensor information using a detection/discrimination method. For example, the detection/discrimination methods could include:

EGM interval-based VT/SVT discrimination method, such as One-Button Detection Enhancement (OBDE). An example of OBDE is described in U.S. Pat. No. 6,317,632, entitled "Apparatus And Method For Treating Ventricular Tachyarrhythmias," which is incorporated herein by reference. Variations of the OBDE method also exist.

EGM morphology-based methods, such as Vector Timing Correlation (VTC). An example of VTC is described in U.S. Pat. No. 6,526,313, entitled "System and method for classifying cardiac depolarization complexes with multi-dimensional correlation," which is incorporated herein by reference. Variations of VTC also exist, for example, more than one template can be used for morphology comparison.

Using an R-wave triggered timing window, the S1 amplitude (|S1|) or the timing (R-S1 duration, $T_{R-S1}$) can be recurrently or continuously monitored, such as by using one or more sensors, such as an accelerometer or an acoustic sensor (e.g., a microphone). The mean and variance of |S1| can be computed, such as over those beats used for computing the VTC. If the variance of |S1| exceeds a preset threshold, AV dysynchrony is declared to have been detected, and the arrhythmia is deemed more likely VT than SVT. Conversely, if the variance of |S1| exceeds a preset threshold, no AV dysynchrony is declared to have been detected, and the arrhythmia is deemed more likely SVT than VT.

The S2 amplitude (|S2|) can be used to determine the aortic pressure variation, thus predicting the hemodynamic stability. In one example, the value of |S2| is recurrently or continuously monitored. The difference between the instantaneous value of |S2| and the mean value is computed. This difference can be expressed as a percentage of a baseline value. The difference is used to compare with a threshold to determine if the arrhythmia is hemodynamically stable.

A pulmonary artery (PA) pressure can be recurrently or continuously monitored using a device such as a separate dedicated implantable Micro Electro Mechanical Sensor (MEMS)-based PA pressure sensor with a wireless communication link to a separate electronics unit of an IMD such as a pacer, defibrillator, or the like. In certain examples, one or more pressure readings during VT are compared to the "normal" range, which is determined during normal sinus rhythm (NSR). If the PA pressure level falls below a certain threshold, such as for some preset time, then the VT is declared to be hemodynamically unstable.

A cardiac output (CO) sensor can be used to measure the cardiac output of a heart during an arrhythmia. For example, a CO sensor can estimate the stroke volume (SV), measure the heart rate, and use this information to determine the CO. A cardiac index (CI) value can be estimated using a formula, such as $CI=CO_{max}/A_{BS}$, where $CO_{max}$ is the maximum CO obtained during a cardiac cycle and ABS is an estimated body surface area. The CO or CI can be used to discriminate between or classify arrhythmias, such as by declaring VT if CO falls below a certain threshold, such as for some preset time.

Figure 5:
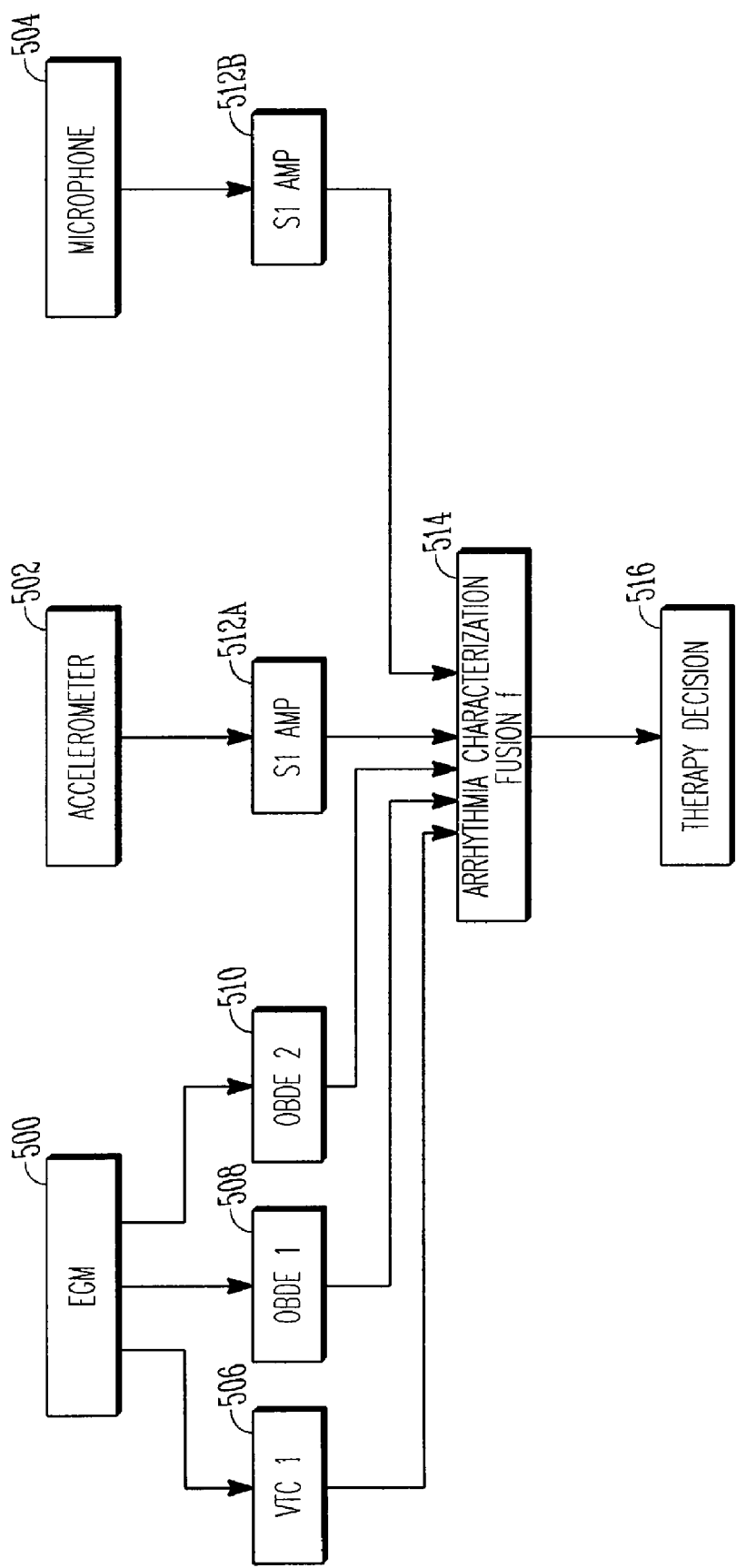
FIG. 5 is a schematic view illustrating an exemplary single-level characterization scheme.

FIG. 5 is a schematic view illustrating an exemplary single-level detection scheme. In this example, a tachyarrhythmia episode has been detected by one or more sensors. As illustrated in FIG. 5, the sensors could include an EGM sensor 500, an accelerometer 502, and a microphone 504. One or more sensors are used by a variety of detectors to discriminate between VT and SVT. In this illustration, the detectors include VTC1 detector 506 (employing a morphology-based discrimination method), OBDE1 detector 508 (employing a rate-based discrimination method), OBDE2 detector 510 (employing a variation of OBDE that targets the 1:1 rhythms using variability of AV and VA intervals during the tachycardia), and S1 detector 512A, 512B (employing a method that analyzes the mean and variance of |S1|). In this example, each detector classifies the tachyarrhythmia and the characterization results are fed into a fusion function 514. At 516, an appropriate therapy is determined and delivered to the patient. In certain examples, the fusion of the separate characterizations is performed using the method 300 described above.

Figure 6:
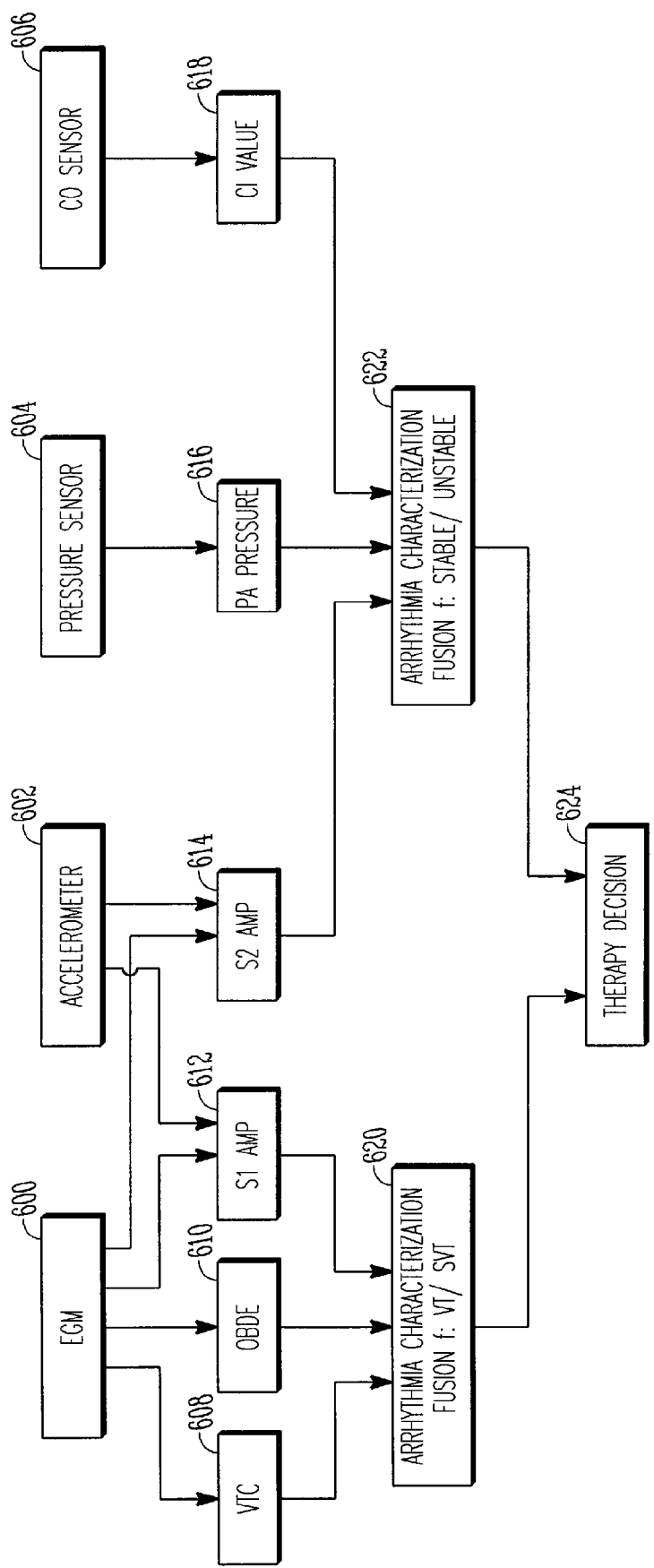
FIG. 6 is a schematic view illustrating an exemplary dual-level characterization scheme.

FIG. 6 is a schematic view illustrating an exemplary dual-level detection scheme. In this illustration, the sensors include an EGM sensor 600, an accelerometer 602, a pressure sensor 604, and a CO sensor 606. In this example, the detectors include VTC detector 608, OBDE detector 610, S1 detector 612, S2 detector 614, PA pressure detector 616, and CI detector 618. In this example, the detectors are grouped into two classes: an arrhythmia detection class and a hemodynamic status detection class. The detectors 608, 610, 612, 614 in the arrhythmia detection class classify the arrhythmia as either VT or SVT, in this example. At 620, the individual detector characterizations are fused. In one example, the fusion method 300 described above is used to produce a secondary or final characterization. The detectors 616, 618 in the hemodynamic status detection class determine if the rhythm is stable or unstable, in this example. At 622, the detector determinations can be fused, for example, by using the fusion method 300 as described above. At 624, an appropriate therapy is determined and delivered to the patient. In one example, a therapy is determined by using the results of the fusions at 620 and 622. In another example, the results of the fusions at 620 and 622 are used to determine another characterization or classification of the arrhythmia, which can then be used to determine the appropriate therapy. In one example, the characterizations found at 620 and 622 are fused, using for example the method 300 as described above.

In some examples, a medical professional can review the sensor data and/or the fused results of the arrhythmia characterization and the hemodynamic stability determination and provide a characterization independent from the fusion results. The independent characterization can be used to adaptively adjust the confidence level of each detector. For example, a confidence level can be raised if the medical professional's independent characterization is similar to or matches the results of the fused characterization and can be lowered if the characterizations are found to be different. In addition, a population database can be used, as described above, to calculate a probabilistic result based on one or more patient indications or one or more other factors, which can then be factored in as a confidence level in future calculations.

Depending on the computational requirements and resources, the fusion of either the arrhythmia characterization and/or the hemodynamic stability can be distributed between the implantable device and an external device. In one example, the fusion is performed in an external device and the result is communicated to the IMD where it is used to determine an appropriate therapy. In one example, the fusion is performed in the IMD while the therapy decision is performed in an external device. At 624, a therapy decision is determined based on the results of the fused characterizations (e.g., from 620 and 622). For example, the fusion results of 620 and 622 could be used to determine a therapy at 624 using a lookup table:

|  | Stable | Unstable |
|---|---|---|
| SVT | Withhold Therapy (Rx) | Anti-tachyarrhythmia Pacing (ATP) |
| VT | ATP + Shock | Shock at maximum energy |

This table can be made more sophisticated by separating the SVT/NVT and/or the stable/unstable characterizations into multiple "soft" levels. For example, one fusion could determine a level of arrhythmia and another fusion could determine a stability level. In another example, the soft levels are represented as percentages or confidence levels (e.g., 80% stability). A method, such as a lookup table, could be used to determine an appropriate therapy. For example:

|  |  | Stability Level | | |
|---|---|---|---|---|
|  |  | 1 | 2 | 3 |
| Arrhythmia | 1 | $Rx_{11}$ | $Rx_{12}$ | $Rx_{13}$ |
| Level | 2 | $Rx_{21}$ | $Rx_{22}$ | $Rx_{23}$ |
|  | 3 | $Rx_{31}$ | $Rx_{32}$ | $Rx_{33}$ |

To calculate the levels of arrhythmia and stability, in certain examples, an m-ary fusion method is used. Similar to the detection scheme illustrated in FIG. 6, each detector outputs two or more local decisions. Each decision is used in two or more fusion functions to determine a fused result. In the sophisticated m-ary version, the fused result is a value, such as representing a degree of arrhythmia or stability. Such degrees are used, such as in the lookup table illustrated above, to derive an appropriately tailored therapy.

In particular, the binary data fusion described above can be extended to m-ary data fusion. Under the m-ary hypothesis testing, the decision space is divided into m mutually exclusive hypotheses $\{H_1, H_2, \ldots, H_m\}$. For example, in the case of an arrhythmia classification there could be five classes, $H_1$=sinus tachyarrhythmia (ST), $H_2$=atrial fibrillation (AF), $H_3$=monomorphic ventricular tachyarrhythmia (MVT), $H_4$=polymorphic ventricular tachyarrhythmia (PVT), and $H_5$=ventricular fibrillation (VF). The fusion problem then becomes: given local decisions from N detectors $\{u_1, u_2, \ldots, u_N\}$, decide which hypothesis maximizes a posterior probability $p(H_i|u_1, u_2, \ldots, u_N)$.

The problem can be reformulated by computing the logarithm of the probability ratios ($L_i$) between $p(H_i|u_1, u_2, \ldots, u_N)$ and $p(H_m|u_1, u_2, \ldots, u_N)$ for i=1, 2, . . . , m−1. Fusion in this m-ary case, assuming $H_1$ to $H_m$ have been determined, can be determined as described below.

First, compute the m−1 log-probability ratio. To do this, we assign $L_m$=0 and for each i=1, 2, . . . , m−1, the log-probability ratio is calculated. Let:

$$L_i = w_{o_i} + \sum_{k=1}^{N} w_{k_i} u_k$$

$$w_{o_i} = \log\left(\frac{P_i}{P_m}\right)$$

$$w_{k_i} = \log\left(\frac{P_{DK} \cdot (m-1)}{1 - P_{KD}}\right)$$

$u_k$=+1 if the decision from detector k assumes $H_i$
$u_k$=−1 if the decision from detector k assumes $H_m$
$u_k$=0 otherwise Second, the fusion decision is made. The characterization $v=H_k$, where $k=\arg\max_{1\leq i\leq m-1}\{L_i\}$. If $L_i<0$ for all $i=1, 2, \ldots, m-1$, then the characterization $v=H_m$.

Figure 7:
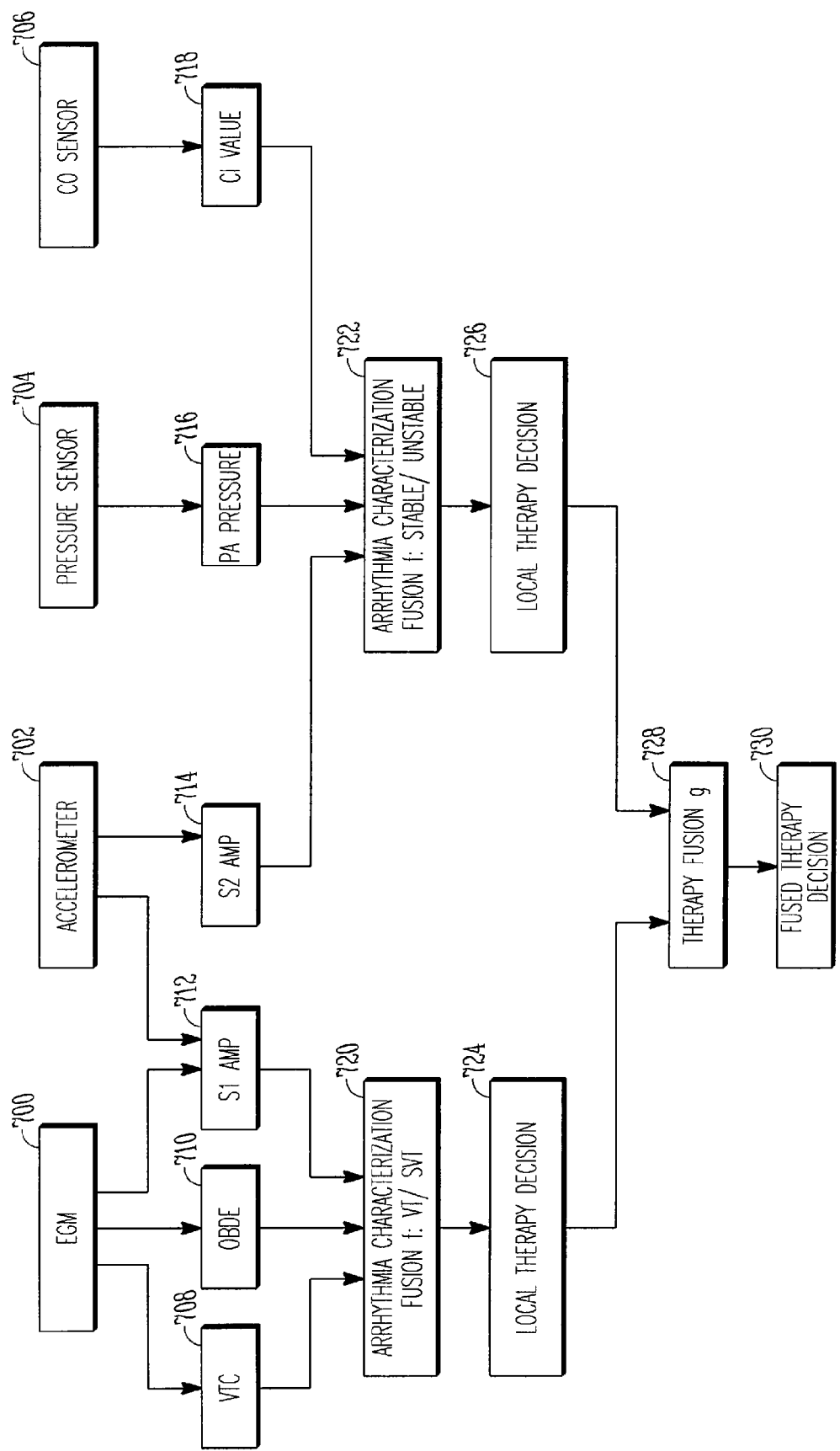
FIG. 7 is a schematic view illustrating another exemplary dual-level characterization scheme.

FIG. 7 is a schematic view illustrating an exemplary dual-level detection scheme. Sensors 700-706 provide signals to detectors 708-718, which characterize aspects of an arrhythmia (e.g., either VT or SVT and whether the rhythm is stable or unstable). At 720, the individual detector characterizations are fused producing a secondary characterization. In one example, the fusion method 300 described above is used to produce the secondary characterization. At 722, the detector determinations can be fused, for example, by using the fusion method 300 as described above. Each characterization fusion 720, 722 is used to determine a local therapy decision 724, 726 based on the corresponding fusion result. For example, if the arrhythmia characterization fusion at 720 found the rhythm to most likely be SVT, then an appropriate corresponding therapy determined at 724 may include anti-tachyarrhythmia pacing (ATP). In certain examples, the arrhythmia characterization is represented as a discrete level (e.g., level 3 SVT) or a percentage of certainty or confidence level (e.g., 70% stable). In a further example, the local therapy decisions include a confidence level that reflects the level of certainty of the corresponding arrhythmia characterization. At 728, the local therapy decisions 724, 726 can be fused, for example, by using the fusion method 300 as described above. In certain examples, the sophisticated m-ary fusion method is used to fuse the local therapy decisions. In an example, a simplified method is used to perform the local therapy decision fusion, such as a lookup table. An example of such a lookup table is illustrated below:

|  |  |  | Stability Level | | |
|---|---|---|---|---|---|
|  |  |  | 1 $Rx_{s1}$ | 2 $Rx_{s2}$ | 3 $Rx_{s3}$ |
| Arrhythmia | 1 | $Rx_{a1}$ | $Rx_{a1}Rx_{s1}$ | $Rx_{a1}Rx_{s2}$ | $Rx_{a1}Rx_{s3}$ |
| Level | 2 | $Rx_{a2}$ | $Rx_{a2}Rx_{s1}$ | $Rx_{a2}Rx_{s2}$ | $Rx_{a2}Rx_{s3}$ |
|  | 3 | $Rx_{a3}$ | $Rx_{a3}Rx_{s1}$ | $Rx_{a3}Rx_{s2}$ | $Rx_{a3}Rx_{s3}$ |
|  | 4 | $Rx_{a4}$ | $Rx_{a4}Rx_{s1}$ | $Rx_{a4}Rx_{s2}$ | $Rx_{a4}Rx_{s3}$ |

In this lookup table, an arrhythmia can be characterized into four discrete levels that indicate, for example, a scale where "Arrhythmia Level 1" represents a most-likely VT condition and "Arrhythmia Level 4" represents a most-likely SVT condition. In such an example, each arrhythmia level has a corresponding therapy ($Rx_a$). Similarly, a hemodynamic stability determination is deconstructed into several degrees or levels. After an arrhythmia level and stability level have been determined, a corresponding therapy is used to determine a fused therapy decision. In alternative examples, a characteristic can be separated into several types instead of degrees of severity. For example, an arrhythmia could be classified into five types of arrhythmia: sinus tachyarrhythmia (ST), atrial fibrillation (AF), monomorphic ventricular tachyarrhythmia (MVT), polymorphic ventricular tachyarrhythmia (PVT), and ventricular fibrillation (VF). Each type of arrhythmia is coupled with a corresponding therapy, where the therapy may change based on the second characterization (e.g., stability level). At 730, an appropriate therapy is determined and delivered to the patient.

In all of the above examples, it is understood that fusion of intermediate results (e.g., characterizations or therapies) using more than two layers is possible.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, various features may be grouped together to streamline the disclosure. This should not be interpreted as intending that the embodiments require more features than are expressly recited in each claim. Rather, as the following claims reflect, inventive subject matter may lie in less than all features of a single disclosed embodiment. Thus the following claims are hereby incorporated into the Detailed Description, with each claim standing on its own as a separate embodiment.

What is claimed is:

1. A machine-assisted method for automatically characterizing a tachyarrhythmia, the method comprising:
   analyzing the tachyarrhythmia at a processor circuit by:
      obtaining from a first detector executing a first tachyarrhythmia characterization technique, a current first primary characterization of the tachyarrhythmia and a current first primary confidence level of the current first primary characterization;
      obtaining from a second detector executing a second tachyarrhythmia characterization technique, a current second primary characterization of the tachyarrhythmia and a current second primary confidence level of the current second primary characterization, wherein the second tachyarrhythmia characterization technique is different from the first tachyarrhythmia characterization technique, and wherein the second detector is different from the first detector; and
      determining a current secondary characterization of the tachyarrhythmia by probabilistically fusing the current first primary characterization, the current first primary confidence level, the current second primary characterization, and the current second primary confidence level.

2. The method of claim 1, wherein obtaining the first or second primary characterization includes analyzing the tachyarrhythmia to discriminate between supraventricular tachycardia (SVT) and ventricular tachycardia (VT).

3. The method of claim 1, wherein obtaining the first or second primary characterization includes analyzing the tachyarrhythmia to determine whether the tachyarrhythmia is hemodynamically stable or unstable.

4. The method of claim 1, comprising using the current secondary characterization to determine a response.

5. The method of claim 4, wherein the response includes one or more of a: shock, no shock, anti-tachyarrhythmia pacing (ATP), or an alert.

6. The method of claim 4, comprising:
obtaining a tertiary characterization using an independent external input; and
adjusting the first primary confidence level and the second primary confidence level using the tertiary characterization.

7. The method of claim 6, comprising forming the independent external input at least in part by using an indication of a medical professional's assessment.

8. The method of claim 6, wherein adjusting the first and second primary confidence levels includes one or more of:
raising the first primary confidence level if the first primary characterization corresponds to the tertiary characterization;
lowering the first primary confidence level if the first primary characterization does not correspond to the tertiary characterization;
raising the second primary confidence level if the second primary characterization corresponds to the tertiary characterization; and
lowering the second primary confidence level if the second primary characterization does not correspond to the tertiary characterization.

9. The method of claim 1, comprising:
obtaining a tertiary characterization using an independent external input;
comparing the tertiary characterization and the secondary characterization; and
using the result of the comparison to determine an accuracy.

10. The method of claim 9, wherein the comparing includes comparing the tertiary characterization to a history of secondary characterizations.

11. The method of claim 9, comprising:
identifying one or more patient indications; and
using the indications to determine a probable characterization by comparing the indications to one or more similar indications that have one or more corresponding known characterizations.

12. The method of claim 11, wherein the obtaining a secondary characterization includes using an independent weight factor determined at least in part using the accuracy and the probable characterization.

13. The method of claim 1, wherein the current first and second primary confidence levels are based at least in part on one or more previous secondary characterizations or one or more previous tertiary characterizations.

14. The method of claim 1, wherein the first tachyarrhythmia characterization technique comprises a first VT/SVT discrimination technique and the second tachyarrhythmia characterization technique comprises a second VT/SVT discrimination technique.

15. The method of claim 1, wherein the first tachyarrhythmia characterization technique comprises a morphology-based VT/SVT discrimination technique and the second tachyarrhythmia characterization technique comprises an interval-based VT/SVT discrimination technique.

16. The method of claim 1, wherein the first tachyarrhythmia characterization technique comprises a first hemodynamic stability determination technique and the second tachyarrhythmia characterization technique comprises a second hemodynamic stability determination technique.

17. A machine-assisted method for automatically characterizing a tachyarrhythmia, the method comprising:
obtaining from a first detector executing a first tachyarrhythmia characterization technique, a first primary characterization of the tachyarrhythmia and a first primary confidence level of the first primary characterization;
obtaining from a second detector executing a second tachyarrhythmia characterization technique, a second primary characterization of the tachyarrhythmia and a second primary confidence level of the second primary characterization, wherein the second tachyarrhythmia characterization technique is different from the first tachyarrhythmia characterization technique, and wherein the second detector is different from the first detector;
obtaining from a third detector executing a third tachyarrhythmia characterization technique, a third primary characterization of the tachyarrhythmia and a third primary confidence level of the third primary characterization;
obtaining from a fourth detector executing a fourth tachyarrhythmia characterization technique, a fourth primary characterization of the tachyarrhythmia and a fourth primary confidence level of the fourth primary characterization, wherein the fourth tachyarrhythmia characterization technique is different from the first, second, and third tachyarrhythmia characterization techniques, and wherein the fourth detector is different from the third detector;
determining a first secondary characterization by probabilistically fusing the first primary characterization, the first primary confidence level, the second primary characterization, and the second primary confidence level; and
determining a second secondary characterization by probabilistically fusing the third primary characterization, the third primary confidence level, the fourth primary characterization, and the fourth primary confidence level.

18. The method of claim 17, comprising determining a tertiary characterization using the first and second secondary characterizations.

19. The method of claim 18, comprising using the tertiary characterization to determine a response.

20. The method of claim 19, wherein the response includes one or more of a: shock, no shock, anti-tachyarrhythmia pacing (ATP), or an alert.

21. The method of claim 17, comprising determining a therapy using at least the first secondary characterization and the second secondary characterization.

22. The method of claim 17, wherein obtaining the first secondary characterization includes analyzing the tachyarrhythmia to discriminate between supraventricular tachycardia (SVT) and ventricular tachycardia (VT), wherein obtaining the second secondary characterization includes analyzing the tachyarrhythmia to determine whether the tachyarrhythmia is hemodynamically stable or unstable, and wherein obtaining the tertiary characterization includes using the first secondary characterization and the second secondary characterization in a weighted formula.

23. A machine-assisted method for automatically characterizing a tachyarrhythmia, the method comprising:
obtaining from a first detector executing a first tachyarrhythmia characterization technique, a first primary characterization of the tachyarrhythmia and a first primary confidence level of the first primary characterization;
obtaining from a second detector executing a second tachyarrhythmia characterization technique, a second primary characterization of the tachyarrhythmia and a second primary confidence level of the second primary characterization, wherein the second tachyarrhythmia characterization technique is different from the first tachyarrhythmia characterization technique, and wherein the second detector is different from the first detector;

obtaining from a third detector executing a third tachyarrhythmia characterization technique, a third primary characterization of the tachyarrhythmia and a third primary confidence level of the third primary characterization;

obtaining from a fourth detector executing a fourth tachyarrhythmia characterization technique, a fourth primary characterization of the tachyarrhythmia and a fourth primary confidence level of the fourth primary characterization, wherein the fourth tachyarrhythmia characterization technique is different from the first, second, and third tachyarrhythmia characterization techniques, and wherein the fourth detector is different from the third detector;

determining a first secondary characterization by probabilistically fusing the first primary characterization, the first primary confidence level, the second primary characterization, and the second primary confidence level;

determining a second secondary characterization by probabilistically fusing the third primary characterization, the third primary confidence level, the fourth primary characterization, and the fourth primary confidence level;

determining a first therapy decision using the first secondary characterization;

determining a second therapy decision using the second secondary characterization; and determining a tertiary therapy decision using the first and second therapy decisions.

24. The method of claim 23, wherein determining the tertiary therapy decision includes using a probabilistic fusion function.

25. A machine-assisted method for automatically characterizing a tachyarrhythmia, the method comprising:

obtaining from a first detector executing a first tachyarrhythmia characterization technique, a current first primary characterization of the tachyarrhythmia and a current first primary confidence level of the current first primary characterization, wherein the current first primary confidence level is based at least in part on an accuracy of a previous first primary characterization;

obtaining from a second detector executing a second tachyarrhythmia characterization technique, a current second primary characterization of the tachyarrhythmia and a current second primary confidence level of the current second primary characterization, wherein the current second primary confidence level is based at least in part on an accuracy of a previous second primary characterization, wherein the second tachyarrhythmia characterization technique is different from the first tachyarrhythmia characterization technique, and wherein the second detector is different from the first detector;

determining a current secondary characterization by probabilistically fusing the current first primary characterization, the current first primary confidence level, the current second primary characterization, the current second primary confidence level, and an independent weight factor, wherein the independent weight factor is a function of a therapy history accuracy and a probable characterization, wherein the probable characterization is based on a correlation between a patient's one or more indications and a population database.

26. The method of claim 25, comprising using the current secondary characterization to determine a response.

27. The method of claim 25, comprising:

obtaining a tertiary characterization using an independent external input; and adjusting the first primary confidence level and the second primary confidence level using the tertiary characterization.

28. The method of claim 27, comprising forming the independent external input at least in part by using an indication of a medical professional's assessment.

29. The method of claim 27, wherein adjusting the first and second primary confidence levels includes one or more of:

increasing the current first primary confidence level if the current first primary characterization is similar or equal to a previous tertiary characterization;

decreasing the current first confidence level if the current first primary characterization is different from the previous tertiary characterization;

increasing the current second primary confidence level if the current second primary characterization is similar or equal to a previous tertiary characterization; or decreasing the current second primary confidence level if the current second primary characterization is different from the previous tertiary characterization.

\* \* \* \* \*